United States Patent [19]
Vogel et al.

[11] Patent Number: 5,637,608
[45] Date of Patent: Jun. 10, 1997

[54] 9-SUBSTITUTED PORPHYCENES

[75] Inventors: Emanuel Vogel; Martin Mueller, both of Cologne, Germany; Otto Halpern, Gerona, Spain; Alexander D. Cross, Atherton, Calif.

[73] Assignee: Cytopharm, Inc., Menlo Park, Calif.

[21] Appl. No.: 418,119

[22] Filed: Apr. 6, 1995

[51] Int. Cl.$^6$ .................. A61K 31/40; C07B 47/00
[52] U.S. Cl. .................. 514/422; 514/183; 514/410; 514/185; 540/145; 424/450
[58] Field of Search .................. 514/422; 424/450; 540/145, 472, 474

[56] References Cited

U.S. PATENT DOCUMENTS

| | | | |
|---|---|---|---|
| 4,721,612 | 1/1988 | Janoff et al. | 424/1.1 |
| 5,244,671 | 9/1993 | Vogel et al. | 514/422 |
| 5,286,474 | 2/1994 | Gust, Jr. et al. | 424/7.1 |

*Primary Examiner*—Robert T. Bond
*Assistant Examiner*—Pavanaram K. Sripada
*Attorney, Agent, or Firm*—Oblon, Spivak, McClelland, Maier & Neustadt, P.C.

[57] ABSTRACT

Novel 9-substituted porphycene compounds are useful in photodynamic therapy.

25 Claims, No Drawings

9-SUBSTITUTED PORPHYCENES

BACKGROUND OF THE INVENTION

1. Field of the Invention

The invention relates to novel porphycene compounds and pharmaceutical compositions containing these compounds which are useful for therapeutic treatment.

2. Discussion of the Background

During the past few years there has developed a widespread recognition that modern, though sophisticated, cancer diagnosis and treatments have served neither to reduce overall the number of cases of reported cancers in the U.S.A. nor, save the notable cases, the death rate. This is a disheartening result for the billions of dollars invested in conquering the disease. Moreover, surgery, radiotherapy and chemotherapy are all associated with major debilitating side effects such as trauma, severe immunosuppression or toxicity which are not easily surmounted by patients already compromised by ill-health.

Early work in the 1970's, followed by rapidly expanding studies in the 1980's, has shown that photodynamic therapy (PDT) offers a viable, less toxic and generally less painful avenue to treatment of cancer. Not all cancers are candidates for PDT. However, neoplasms of hollow organs and skin, including multifocal carcinoma in situ, sometimes inoperable, and with no good track record for treatment by established therapeutic procedures, appear to be targets for PDT.

In photodynamic therapy, porphyrinoid dyes are administered to a patient and localize in neoplastic tissues (Lipson et al., *J. Thoracic Cardiovascular Surgery*, 1961, 42:623–629). Irradiation of the porphyrinoid dye with light at a wavelength which corresponds to an absorption band of the dye results in destruction of the neoplastic tissue. See also Kessel, D., "Methods in Porphyrin Photosensitization", Plenum Press, New York, 1985; Gomer, C. J., "Photodynamic Therapy", Pergammon Press, Oxford, 1987 and Doiron, D. R. and Gomer, C. J., "Porphyrin Localization and Treatment of Tumors", Liss, New York, 1984. The use of a fiber optic laser light source is described in U.S. Pat. No. 4,957,481.

Dougherty et al. (*Cancer Res.*, 1978, 38:2628; Photochem. Photobiol, 1987, 45:879) pioneered the field with infusion of photoactivatable dyes, followed by appropriate long wavelength radiation of the tumors (600+nm) to generate a lethal short-lived species of oxygen which destroyed the neoplastic cells. Early experiments utilized a mixture termed hematoporphyrin derivative (HPD). See also Lipson et al., *J.N.C.I.*, 1961, 26:1; Dougherty et al., *J.N.C.I.*, 1975, 55:115; Diamond et al., Lancet, 1972(II), 1175; D. Dolphin, "The Porphyrin", vol. I, Academic Press, New York, 1978; and D. Kessel, Photochem. Photobiol., 1984, 39:851. The deficiencies of HPD, especially prolonged phototoxicity caused by retained HPD components in human skin led to its displacement by a purified fraction initially termed dihematoporphyrin ether (DHE), and later marketed by QuadraLogics Technologies as the commercial product "PHOTOFRIN", which, although yielding improvements over HPD, nevertheless still suffered certain practical limitations. Relatively weak absorption in the wavelength range above 600 nm, retention in dermal cells (potentially leading to phototoxicity), only modest or low selectivity for tumor cells versus other cell types in vital organs, the inability to use available, modern, inexpensive diode lasers, and uncertain chemical constitution of the mixtures are all known negative features of PHOTOFRIN and HPD. The great majority of the earlier PDT agents studied have been derived from natural sources (porphyrin, chlorins, purpurins, etc.) or from known chemicals originating in the dyestuffs industry (e.g., cyanine dyes). For more recent PDT agents derived from natural sources see U.S. Pat. No. 4,961,920 and U.S. Pat. No. 4,861,876.

In animal and cell culture experiments one observes, following PDT, depending on the incubation time, damage to the vasculature, cell membranes, mitochondria and specific enzymes. When absorbed in tumor cells, an increased selectivity can be obtained by injecting the porphyrinoid sensitizers enclosed in liposomes (Ricchelli and Jori, Photochem. Photobiol., 1986, 44:151). Porphyrinoid dyes can be transported in the blood with the aid of lipoproteins such as low-density lipoprotein (Jori et al., Cancer Lett., 1984, 24:291).

PDT has been used to treat bladder, bronchial, bone marrow and skin tumors (Dougherty, Photochem. Photobiol., 1987, 45:879, Sieber et al., Leukemia Res., 1987, 11:43) as well as severe psoriasis (Diezel et al., Dermatol. Monatsschr., 1980, 166:793; Emtenstam et al., Lancet, 1989 (I), 1231). Treatment of viruses in transfused blood has also been reported (Matthews et al., Transfusion, 1988, 28.81; Sieber et al., Semin. Hematol., 1989, 26:35).

As the deficiencies of earlier PDT agents have become apparent, it also becomes possible to define activity parameters for improved chemically pure photoactivatable dyes for PDT therapy, available by chemical synthesis. Moreover, the products of synthesis lend themselves more readily to further chemical structural manipulation than do the naturally occurring starting materials which can be expensive and bear chemically sensitive constituents. The synthesis of novel porphycene macrocycles embracing four pyrrole rings has been described by Vogel and coworkers. Alkylated porphycenes have also been prepared (R=Me, Et, n-Pr, tert. butyl, phenyl) and the photochemical properties determined. The potential suitability of these compounds for PDT was noted and confirmed in animal studies (Guardiano et al., Cancer Letters, 1989, 44, 1).

Synthetic efforts have focused on porphryinoid compounds which are highly absorptive in the longer wavelength range of about 660–900 nm, where the transparency of tissue is higher. compounds such as purpurines (Morgan et al., *J. Org. Chem.*, 1986, 51:1347; Morgan et al., *Cancer Res.*, 1987, 47:496; Morgan et al., *J. Med. Chem.*, 1989, 32:904; Hoober et al., Photochem. Photobiol., 1988, 48:579), naphthocyanin silicon complexes (Firey et al., *J. Am. Chem. Soc.*, 1988, 110:7626), chlorins (Robert et al., J.N.C.I., 1988, 80:330; Kessel, *Cancer Res.*, 1986, 46:2248), bacteriochlorins (Beams et al., Photochem. Photobiol., 1987, 46:639) and substituted phenylporphyrins (Kreimer-Birnbaum, Semin. Hematol., 1989, 26:157) have been prepared and tested in vivo. Additional PDT agents are described in EP 276,121.

Pyrrole-containing ring systems larger than porphycene have also been prepared and evaluated as photosensitizers. Sessler et al. have prepared and studied texaphyrin (*J. Am. Chem. Soc.*, 1988, 110:5586) and Woodward et al. and Johnson et al. have prepared and investigated the sapphyrin ring system. Additionally, the platyrin system has been studied by LeGoff (Tetrahedron, Lett., 1978, 4225; *J. Org. chem.*, 1987, 710) and vinylogous porphyrins have been studied by Franck (Angew. Chem., 1986, 98:1107; Angew. Chem. Int. Ed. Eng., 1986, 25:1100; Angew. Chem., 1988, 100:1203; Angew. Chem. Int. Ed. Eng., 1988, 27:1170).

A need continues to exist, therefore, for new compounds for use in PDT therapy, which compounds are easily available, have low intrinsic toxicity, are efficient photosensitizers for single oxygen production, have selective uptake in rapidly proliferating cells, are rapidly or at least moderately rapidly degraded and eliminated from the tissues after administration and which are available as chemically pure and stable compounds easily subject to synthetic modification. The compound should be capable of formulation to allow transdermal delivery if targeted for topical application.

SUMMARY OF THE INVENTION

Accordingly, one object of the present invention is to provide new and effective compounds for use in photodynamic therapy whose properties and characteristics approach the ideal characteristics of PDT dyes listed above.

This and other objects which will become apparent from the following specification have now been achieved with the compounds of the present invention. The present compounds have utility as PDT dyes for use in cancer therapy and dermatological diseases, i.e., psoriasis, etc.

DETAILED DESCRIPTION OF THE PREFERRED EMBODIMENTS

The porphycene compounds of the present invention have the structure shown below.

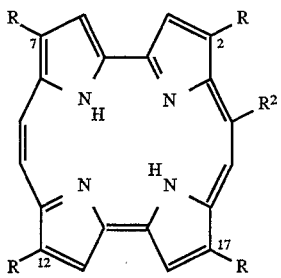

In this structure each R in the 2, 7, 12, and 17-positions of the porphycene structure is, independently of one another, hydrogen, alkyl, aralkyl or aryl.

In the structure shown above, $R^2$ may be $-OC(O)R^3$, where $R^3$ is $-(CH_2)_m-Y$, m=1–10, preferably 1–6, and Y is:

(a) halogen (F, Cl, Br, I), (b) $COOR^4$, where $R^4$ is hydrogen, alkyl, aryl, aralkyl, cycloalkyl or cycloalkylalkyl, (c) $NR^5R^6$, where $R^5$ and $R^6$ independently, are hydrogen, alkyl, aryl; aralkyl, cycloalkyl or cycloalkylalkyl, or $R^5$ and $R^6$ taken together with the nitrogen atom to which they are attached are a 3–7 membered saturated or unsaturated heterocyclic ring optionally containing an additional O, $NR^4$ or S ring member, and $R^4$ is as defined above, (d) $NR^4R^5R^{6+}A^-$, where $A^-$ is an anion and $R^4$, $R^5$ and $R^6$ are as defined above, (e) $NH-C(O)OR^4$, where $R^4$ is as defined above.

In further embodiments, $R^2$ may be $-OC(O)R^7$, where $R^7$ is $-CHR^8=CHR^9-R^{10}$, $R^8$ and $R^9$ are, independently, hydrogen or $C_{1-6}$ alkyl and $R^{10}$ is alkyl, cycloalkyl, cycloalkylalkyl, aralkyl or aryl. $R^7$ may also be an aryl group having 1–3 substituents including halogen, haloalkyl, nitro, cyano, $C_{1-6}$ alkyl, $C_{1-6}$ alkoxy and $C_{2-6}$ alkoxycarbonyl groups.

In another embodiment $R^2$ may be $NR^{11}R^{12}$, where $R^{11}$ and $R^{12}$, independently, are cycloalkyl or cycloalkylalkyl groups. $R^2$ may also be a $NHCO-(CH_2)_p-Z$, $NHCO-O(CH_2)_p-Z$ or $NH(CH_2)_{p+1}-Z$ group, where p=1–10, preferably 1–6, and Z is OH, $NR^{11}R^{12}$, $C(O)OR^4$, $OC(O)R^4$, $C(O)NHR^4$ or $NHC(O)OR^4$, where $R^4$ is as defined above.

To improve water solubility, the porphycene compounds may be further bonded to amino acids, peptides, monosaccharides or oligosaccharides. Generally, the porphycene compounds are bonded to an amino acid or peptide through a free hydroxyl, amino or carboxy group on the porphycene using conventional condensation reactions. Similarly, the porphycenes may be bonded to glycosides using well known chemistry. Additionally, the porphycene compounds may be bonded to carotenoids to provide compounds which fluoresce and are useful as tumor diagnostic agents.

Suitable alkyl groups within this invention are straight-chain or branched alkyl groups. Preferably, the alkyl groups have 1–10 carbon atoms, more preferably 1–6 carbon atoms. Examples include methyl, ethyl, n-propyl, i-propyl, n-butyl, i-butyl, t-butyl, n-pentyl, ethylhexyl, decyl, etc.

Suitable cycloalkyl groups include cycloalkyl groups having 3–7 ring atoms, preferably cyclopropyl, cyclopentyl, cyclohexyl and cycloheptyl groups. These cycloalkyl groups may be unsubstituted or may be substituted with one or more alkyl substituents, generally from 1 to 3 alkyl groups having 1–6 carbon atoms.

Suitable cycloalkylalkyl groups include the cycloalkyl groups described above bonded to a straight-chain or branched alkyl group, preferably an alkyl group having 1–10 carbon atoms.

Suitable aryl groups include $C_{6-20}$ carbocyclic aryl groups, optionally substituted, preferably with one or more $C_{1-6}$ alkyl groups. Examples include phenyl, naphthyl, indenyl, etc. Arylene groups ($C_6H_4$) may be ortho-, meta- or para- substituted, preferably para-substituted.

Suitable aralkyl groups are the aryl groups defined above bonded to a $C_{1-6}$ alkylene group. Examples include benzyl, phenylethyl, phenylpropyl, phenylbutyl, etc.

Suitable amino acids are the 20 naturally occurring amino acids, i.e., phenylalanine, leucine, serine, tyrosine, alanine, glycine, cysteine, tryptophan, proline, histidine, arginine, glutamine, isoleucine, methionine, threonine, asparagine, lysine, valine, aspartic acid, glutamic acid. Suitable peptides include two or more of these amino acids, preferably 2–10, more preferably 2–6 amino acids bonded together through amide bonds.

Monosaccharides which may be bonded to the porphycene compounds of the present invention include both pentose and hexose saccharides including glucose, mannose, galactose, fructose, etc. Similarly, oligosaccharides containing a plurality of monosaccharide units, preferably 2–6 saccharide units, more preferably 2–3 saccharide units may be bonded to the porphycene compound.

Suitable carotenoid substituents have the structure (III) shown below.

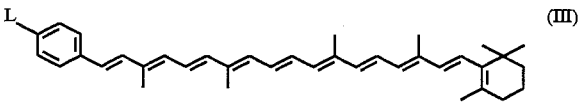

In this structure, L is a linking group through which the carotenoid substituent is bonded to the porphycene ring structure. Suitable linking groups L include $-OC(O)-$ and $-NHC(O)-$.

Particularly, preferred compounds contain four identical R substituents. In these preferred compounds, R is most preferably $-(CH_2)_n-H$ and n=1–6.

Preferred substituents $R^2$ are $OCOR^3$, where $R^3$ is $-(CH_2)_m-Y$, m=1–6 and Y is halogen (preferably Cl or Br), COOR$^4$ where R$^4$ is C$_{1-6}$ alkyl, NH$_2$ and NHC(O)OR$^4$ where R$^4$ is C$_{1-6}$ alkyl. Additional preferred substituents R$^2$ are —NHCO(CH$_2$)$_p$—Z where p=1–6 and Z is OH, NH$_2$, COOH, or OCOR$^4$, where R$^4$ is C$_{1-6}$ alkyl. Also preferred are compounds in which R$^3$ is —C$_6$H$_4$—OR$^4$ or —C$_6$H$_4$—C(O)OR$^4$, where R$^4$ is an alkyl group having 1–6 carbon atoms. When R$^7$ is —CR$^8$=CR$^9$—R$^{10}$, R$^8$ and R$^9$ are preferably hydrogen and R$^{10}$ is preferably phenyl. The phenyl group may be unsubstituted or substituted with 1–5, preferably 1–2 C$_{1-6}$ alkyl groups, preferably straight-chain alkyl groups.

The anion A$^-$ may be any pharmaceutically acceptable anion including, but not limited to inorganic anions such as chloride, sulfate, phosphate, diphosphate, bromide and nitrate and organic anions such as acetate, malate, maleate, fumarate, tartrate, succinate, citrate, lactate, methanesulfonate, p-toluenesulfonate, palmoate, salicylate and stearate.

The porphycenes are prepared by coupling appropriately substituted dialdehydes to form the porphycene ring structure and further modification of the resulting porphycene. Synthesis of suitable porphycene starting materials are described in U.S. Pat. No. 5,244,671. This patent is incorporated herein by reference in its entirety to provide a more complete description of how to prepare suitable porphycenes.

Acyloxy compounds of the present invention may be prepared by reacting a suitable porphycene precursor having the formula (I)

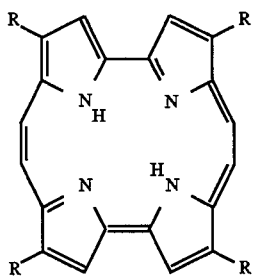

(I)

with an organic acid of the formula (II)

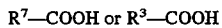

R$^7$—COOH or R$^3$—COOH    (II)

where R$^3$ and R$^7$ are as defined above, in the presence of lead oxide (PbO$_2$) or manganese oxide (MnO$_2$) The reaction is generally conducted in organic aprotic solvents such as halogenated hydrocarbons (e.g., chloroform, methylene chloride) or acetonitrile. The tetrasubstituted porphycene precursor is stirred with the lead oxide or manganese oxide for a period of time sufficient to complete the reaction forming compounds of the invention in which R$^2$ is OC(O)R$^3$ or OC(O)R$^7$. Generally, about equimolar amounts of the starting tetrasubstituted porphycene and the lead oxide or manganese oxide are combined together with a slight excess of the organic acid in the solvent and stirred at room temperature. The specific reaction time depends upon the acid used and whether or not lead oxide or manganese oxide is used. Reactions with lead oxide are generally faster than the corresponding reactions with manganese oxide. Reaction times ranging from about 20 minutes to about 10 weeks are generally necessary to produce the desired 9-substituted products. The resulting reaction mixture is then poured into a dilute aqueous base solution, e.g. aqueous NaHCO$_3$, and may be purified by extraction, chromatography, recrystallization, etc. according to known procedures.

Terminal amides and esters in R$^3$ can be selectively hydrolysed to the corresponding amine or carboxylic acid using appropriate conventional acid hydrolysis conditions.

The compounds of the present invention in which R$^2$ is —NHCO—(CH$_2$)$_p$—Z are prepared by reacting the tetrasubstituted porphycene precursor identified above with silver nitrate and acetic acid to form the corresponding nitro tetrasubstituted porphycene. The nitro derivative is then reduced with sodium dithionite/sodium hydroxide to produce the corresponding amino derivative. Suitable synthetic procedures are described in U.S. Pat. No. 5,244,671. The 9-amino-porphycene can be reacted with an acid halide having the formula Hal—CO—(CH$_2$)$_p$—Z where Z is C(O)OR$^4$ or C(O)NHR$^4$. This reaction is generally conducted in a polar aprotic solvent such as tetrahydrofuran (THF) containing a base such as pyridine. The terminal ester or amide group may be selectively hydrolyzed to the corresponding carboxylic acid by alkaline or acid hydrolysis, e.g. NaOH/CH$_3$OH/THF or NaOCH$_3$/CH$_3$OH/THF. The terminal ester group may also be reduced to the corresponding alcohol using, for example, a metal hydride reduction (e.g. LiAlH$_4$/THF or LiBH$_4$/THF).

The compounds of the present invention in which R$^2$ is —NH(CH$_2$)$_{p+1}$—Z can be prepared by reducing the carbonyl of the —NHCO(CH$_2$)$_p$—Z group using conventional reduction reactions.

Porphycene compounds bonded to amino acids, proteins, monosaccharides or oligosaccharides are prepared using known reactions. See U.S. Pat. No. 5,244,671, incorporated herein by reference.

Carotenoid derivatives of the porphycene compounds of the present invention are prepared by forming carotenoid compounds in which L is an acid halide, for example an acid chloride, having a structure Cl—C(O)— and reacting the carotenoid acid halide with a porphycene having a hydroxy or amino group at the 9-position.

Metal complexes containing divalent metals, preferably complexes of smaller metals such as zinc, nickel, magnesium, tin, etc., and the porphycene compounds of the present invention can be easily prepared by the addition of metal salts, e.g., metal acetates, to the porphycene compounds in acid medium, such as glacial acetic acid. Demetallation occurs when the metal complex is reacted with concentrated sulfuric acid at room temperature with stirring. Hydrogen ions displace the metal atom during the demetallation reaction (Buchler, J. W. in Smith, K. M. (Ed): "Porphyrin and Metalloporphyrin", Elsevier, Amsterdam, 1975; Buchler, I. W. in Dolphin, D. (Ed), "The Porphyrin," Vol. I, Academic Press, New York, 1978; Dorough et al., *J. Am. Chem. Soc.*, 1951, 73:4315).

The invention also includes pharmaceutically acceptable acid and base addition salts of the porphycene compounds which may be prepared by the known addition of acids such as HCl, HBr, H$_2$SO$_4$, H$_3$PO$_4$, malic acid, tartaric acid, maleic acid, fumaric acid, etc. Base addition salts are prepared by the addition of alkali and alkaline earth metal salts such as sodium, potassium, calcium and magnesium carbonates, bicarbonates, sulfates, phosphates, etc. as well as by addition of ammonia, amines, preferably primary, secondary and tertiary C$_{1-6}$ alkyl amines, amino acids, etc. Any conventional acid or base addition salt which is pharmaceutically acceptable is considered to be within the scope of the present invention.

The porphycene compounds of the present invention may be formulated as therapeutic formulations for administration to patients in need of photodynamic therapy.

THERAPEUTIC FORMULATIONS

Therapeutic compositions containing the compounds of the present invention include liposome or microvesicle preparations, dispersions, solutions for parenteral injection, etc. and including topical dermatological preparations.

Parenteral Solutions

The photoactivatable porphycene dyes generally are used with additional solvents and adjuvants to prepare solutions suitable for intravenous injection. A number of solvents and co-solvents that are miscible with water and suitable surfactants can be used to achieve solutions for parenteral use. The most important solvents in this group are ethanol, polyethylene glycols of the liquid series and propylene glycol. A more comprehensive listing includes acetone, dimethyl acetamide, dimethyl formamide, dimethyl sulfoxide ethanol, glycerin, polyethylene glycol 300, and 400, propylene glycol, sorbitol, polyoxyethylene sorbitan fatty acid esters such as laureate, palmitate, stearate, and oleate, polyoxyethylated vegetable oil, sorbitan monopalmitate, 2-pyrrolidone; n-methyl-2-pyrrolidine; n-ethyl-1-pyrrolidine; tetrahydrofurfuryl alcohol, tween 80 and dimethyl isosorbide. Dimethyl isosorbide (ARLASOLVE® DMI, ICI Specialty Chemicals) has the advantage of being both water- and oil-soluble. Additionally, dimethyl isosorbide may be readily gelled with a gelling agent to produce gel formulations with, for example, 4% KLUCEL® (Hercules).

Other additives may be necessary to enhance or maintain chemical stability and physiological suitability. Examples are antioxidants, chelating agents, inert gases, buffers and isotonicifiers.

Examples of antioxidants and typical concentration ranges include acetone sodium bisulfite (0.1–0.8%), ascorbic acid (0.05–1.0%), monothioglycerol (0.1–1.0%), potassium metabisulfite (0.05–0.1%), propyl gallate (0.02%), sodium bisulfite (0.01–1.0%), sodium formaldehyde sulfoxylate (0.03–0.1%), sodium metabisulfite (0.02–0.25%), sodium sulfite (0.01–0.1%), sodium thioglycolate (0.05–0.1%).

Examples of chelating/complexing agents and typical concentration ranges include edetate sodium (0.005–0.1%), edetate calcium disodium (0.005%–0.01%), gentisic acid ethanolamide (1.0%–2.0%), niacinamide (1.0%–2.5%), sodium citrate (0.01%–2.5%), citric acid (0.001%–1.0%).

Examples of inert gases are nitrogen and carbon dioxide.

Buffers are used primarily to stabilize a solution against the chemical degradation that might occur if the pH changed appreciably. Buffer systems employed normally have as low a buffer capacity as feasible in order to not disturb significantly the body buffer systems when injected. The buffer range and effect of the buffer on activity must be evaluated. Appropriate adjustment is useful to provide the optimum conditions for pH dependent partition into the target malignant tissues or lesion area.

Examples of such buffer systems include the following acids: acetic, adipic, ascorbic, benzoic, citric, glycine, lactic, tartaric, hydrochloric, phosphoric, sulfuric, carbonic and bicarbonic; and their corresponding salts such as: potassium, sodium, magnesium, calcium and diethanolamine salts.

Osmoticity is of great importance and hypotonic solutions usually have their tonicity adjusted by the addition of salts such as sodium chloride, potassium chloride, magnesium chloride and calcium chloride and sugars such as dextrose, lactose, mannitol and sorbitol.

When the solution will be dispensed from multiple dose containers, antimicrobial agents in bacteriostatic or fungistatic concentrations must be added. Among the compounds and concentrations most frequently employed are phenylmercuric acid (0.002–0.01%), thimerosal (0.01%), benzethonium chloride (0.01%), benzalkonium chloride (0.01%), phenol or cresol (0.5%), chlorbutanol (0.5%), benzyl alcohol (2.0%), methyl p-hydroxybenzoate (0.18%), and propyl p-hydroxybenzoate (0.02%).

After the solution of the porphycene with its solvents and additives has been compounded, the solution is generally filtered to remove particulate matter above 24 μm in size and a further step eliminating particulate matter down to 0.2 μm can eliminate microorganisms and accomplish cold sterilization. The solution is filled under aseptic conditions. The final solution can be additionally sterilized in its final container by thermal methods such as autoclaving or non-thermal methods such as ionizing radiation. The process of freeze drying (lyophilization) can be employed to avoid adverse thermal and oxidative decomposition and provide enhanced stability and improved solubility.

Topical Formulations

The porphycene compounds of the present invention may be formulated for topical application in penetrating solvents or in the form of a lotion, cream, ointment or gel containing a sufficient amount of the porphycene compound to be effective for PDT therapy.

Suitable penetrating solvents are solvents for the porphycene compound which will enhance percutaneous penetration of the porphycene compound. Solvents which have this property include dimethyl sulfoxide, dimethyl acetamide, dimethylformamide, 1-methyl-2-pyrrolidone, diisopropyladipate, diethyltoluamide and to a lesser extent propylene glycol. Additional solvents include substituted azacycloalkan-2-ones having from 5 to 7 carbons in the cycloalkyl group such as 1-dodecylazacycloheptan-2-one (AZONE) and other azacycloalkan-2-ones such as described in U.S. Pat. No. 3,989,816 incorporated herein by reference.

Also included are N-bis-azocyclopentan-2-onyl alkanes described in U.S. Pat. No. 3,989,815 (hereby incorporated by reference), 1-substituted azacyclopentan-2-ones described in U.S. Pat. No. 3,991,203 (hereby incorporated by reference) and water-soluble tertiary amine oxides described in U.S. Pat. No. 4,411,893 (hereby incorporated by reference).

The topical formulations contain a sufficient amount of the porphycene compound to be effective in PDT therapy. Generally, concentrations in the range of 0.001 to 5 wt. %, preferably from about 1 to 5 wt. %, may be used. Typical lotion and cream formulations are shown below.

Additional topical formulations which may be used in conjunction with the porphycene compounds of the present invention are disclosed in U.S. Pat. No. 3,592,930 and U.S. Pat. No. 4,017,615 (hereby incorporated by reference).

Topical formulations may be prepared in gel form by combining the porphycene with a solvent such as alcohol, dimethyl sulfoxide, propylene carbonate, diethyltoluamide (DEET), diisopropyl adipate (DIPA), etc. and adding a gelling agent. A preferred gelling agent is fumed silica (CAB-O-SILO®, Cabot Corp., Tuscola, Ill.), and particularly grade M-5. The gelling agent is generally used in amounts of about 5–12 wt% to obtain a gel with the desired viscosity. Obviously, gels containing more or less gelling agent will have slightly higher or lower viscosity. One skilled in the art can readily obtain the desired gel viscosity by adjusting the concentration of gelling agent. Additives, such as cosolvents and/or surfactants, frequently improve the gel properties and may be added as desired. Suitable cosolvents/surfactants include propylene glycol and glycerine. The additives may be incorporated into the gel by mechanically mixing the additives into a mixture of solvent and gelling agent.

Liposome or Microvesicle Preparations

Liposomes and methods of preparing liposomes are known and are described for example in U.S. Pat. No. 4,452,747 and U.S. Pat. No. 4,448,765 incorporated herein by reference. Liposomes are microvesicles which encapsulate a liquid within lipid or polymeric membranes. The porphycene compounds of the present invention may be incorporated into liposome microvesicles and used in this form for both topical and parenteral application. Topical and parenteral liposome preparations are known in the art. Sonified unilamellar liposomes made from certain unsaturated lipids are known stable carriers for some of the porphycenes of the invention.

U.S. Pat. No. 4,837,028 discloses injectable liposome formulations having enhanced circulation time. The liposomes have a size of about 0.08–0.5 microns, contain at least 50 mole % of a membrane rigidifying component such as sphingomyelin and further contain about 5–15 mole % ganglioside $G_{M1}$. Liposome preparations for encapsulating sparingly soluble pharmaceutical compounds are disclosed in U.S. Pat. No. 4,721,612. The specification of these U.S. patents is incorporated herein by reference.

After administration of a therapeutically effective amount of one or more of the porphycene compounds in the pharmaceutical composition or preparation, to a patient having a treatable condition such as a solid tumor (cancer) or psoriasis, for example, the patients affected body area is exposed to a therapeutically sufficient amount of light having an appropriate wavelength for absorption by the particular porphycene compound used. Suitable wavelengths are generally from about 600 to about 900 nm, preferably from about 600 to about 700 nm. Irradiation of the accumulated porphycene usually generates singlet oxygen which is thought to be the actual lethal species responsible for destruction of the neoplastic cells.

Photodynamic therapy using the porphycene compounds of the present invention has a number of advantages. The porphycene compound itself is minimally toxic in the unexcited state. Each porphycene molecule can be repeatedly photoactivated and leads 40–60% of each time to cell-lethal events, that is, the generation of singlet molecular oxygen. The half-life of singlet molecular oxygen is approximately four microseconds in water at room temperature. The target cell is therefore affected without the opportunity for migration of the lethal singlet molecular oxygen to neighboring healthy tissue cells. Preferably, the singlet oxygen molecules rupture chemical bonds in the target cell wall or mitochondria resulting in destruction of the target cell. Destruction of target cell tissue commences promptly upon irradiation of the porphycene compounds. Indirect target cell death can also result from destruction of the tumor vascular system with concomitant restriction of oxygen supply.

Photodynamic therapy using the compounds of the present invention is therefore selective and minimally toxic to healthy tissue. Singlet oxygen molecules produced which do not react rapidly decay to harmless ground state oxygen molecules.

A variety of phototherapy and irradiation methodologies are known to those skilled in the art and can be used with the novel porphycene compounds of the present invention. The time and duration of therapy and repetition of the irradiation treatment can be selected by the therapist (physician or radiologist) according to known photodynamic therapy criteria. The dosage of the porphycene compound may be varied according to the size and location of the target tissues which are to be destroyed and the method of administration. Generally, the dosage will be in the range of 0.05–10 mg of porphycene compound per kilogram of body weight, more preferably in the range of 0.1–5.0 mg/kg.

Irradiation generally takes place not less than two minutes nor more than four days after parenteral administration of the porphycene compound. Usually, phototherapy is begun approximately about 5 minutes to about 24 hours after systemic administration for the tetraalkyl porphycenes. With topically administered dye, radiation may commence as soon as 3 minutes after dye application for treatment of psoriasis, genital warts, bacterial infections, etc., but radiation up to 24 hours after due administration may be preferred according to individual dye incorporation properties. Exposure to non-therapeutic light sources should be avoided immediately following phototherapy to minimize light toxicity. Appropriate draping of the patient can be used to limit the area affected by phototherapy.

Light sources which are appropriate for use are well known in the art and may vary from non-coherent light sources with appropriate filters to lasers. As noted above, preferred wavelengths are from 600 to 900 nm, preferably from about 600 to about 700 nm. The total amount of light which is applied to the affected area will vary with the method used and the location of the tumor or topical lesion. Generally, the amount of light is in the range of about 10 to 300 $J\text{-}cm^2$ preferably in the range of 20 to 200 $J\text{-}cm^2$.

Having generally described this invention, a further understanding can be obtained by reference to certain specific examples which are provided herein for purposes of illustration only and are not intended to be limiting unless otherwise specified. Procedures which are constructively reduced to practice herein are described in the present tense and procedures which have been carried out in the laboratory are set forth in the past tense.

EXAMPLES

Example 1—9-(Glutaroxy-t-butylester)-2,7,12,17-tetra-n-propylporphycene

A solution of 478 mg (1.0 mmol) 2,7,12,17-tetra-n-propylporphycene (TPPn) in 50 ml $CH_2Cl_2$ and 7 g glutaric acid mono-t-butylester was combined with 239 mg (1 mmol) $PbO_2$ and stirred for 24 h at room temperature. The reaction mixture was treated with 100 ml $CH_2Cl_2$ and then poured into 200 ml 5% aqueous sodium hydrogen carbonate and extracted with an additional 100 ml dichloromethane. After washing the organic phase once with 150 ml of 5% aqueous sodium hydrogen carbonate and twice with 200 ml water, the organic layer was separated and evaporated under vacuum. The residue was chromatographed with dichloromethane/n-hexane (1:1) on silica gel (column =45×5 cm). The first eluted compound consisted of unchanged tetra-n-propylporphycene, crystallized from $CH_2Cl_2$/n-hexane affording 259 mg. Following evaporation of the solvent and crystallization of the residue of the next large fraction of $CH_2Cl_2$/n-hexane, the title compound 9-(glutaroxy t-butylester)-tetra-n-propylporphycene was obtained in the form of small, blue needles having a melting point of 131°–132° C. Yield: 152 mg, 22.9% (based on recovered TPPn: 50%)

Example 2—9-Glutaroxy-2,7,12,17-tetra-n-propylporphycene 100 mg (0.15 mmol) of 9-(glutaroxy-t-butylester)-tetra-n-propylporphycene was dissolved in 8 ml 90% trifluoroacetic acid and stirred for 40 minutes at room temperature. The solution was combined with 120 ml diethylether and then with 75 ml n-hexane. From this solution, the product crystallized in small fibrous needles by losing slowly at room temperature small amounts of the diethylether from the solvent mixture. The product was filtered off and washed with a solvent mixture of diethylether/n-hexane (1:1). Yield : 81 mg (888), melting point: 184°–186° C.

Example 3—9-(N-BOC-4-aminobutyroxy)-2,7,12,17-tetra-n-propylporphycene

A solution of 478 mg (1 mmol) of TPPn in 80 ml $CH_2Cl_2$ and 7 g N-BOC-4-aminobutyric acid was combined with 239 mg (1 mmol) $PbO_2$ and stirred for three days at room temperature. The mixture was then poured into 300 ml water and extracted with 250 ml dichloromethane. After washing the organic phase once with 150 ml of 5% aqueous sodium hydrogen carbonate and twice with 200 ml water, the separated organic layer was evaporated under vacuum. The residue was chromatographed with dichloromethane/n-hexane (4:1) on silica gel (column=40×5 cm). The first eluted fraction consisted of unchanged TPPn crystallized from dichloromethane/n-hexane affording 310 mg. Following evaporation of the solvent and crystallization of the residue of the next large fraction from $CH_2Cl_2$/n-hexane, the title compound was obtained in the form of small, blue needles having a melting point of 178°–179° C. Yield : 119 mg, 17.4% (based on recovered TPPn: 49%).

Example 4—9-(N-BOC-5-aminovalerianoxy)-2,7,12,17-tetra-n-propylporphycene

A solution of 175 mg (0.37 mmol) TPPn in 15 ml $CH_2Cl_2$ and 1 g N-BOC-5-aminovaleric acid was combined with 88 mg (0.37 mmol) $PbO_2$ and stirred for five days at room temperature. The reaction mixture was then poured into 100 ml water and extracted with 100 ml dichloromethane. After washing the organic phase once with 50 ml of 5% aqueous sodium hydrogen carbonate and twice with 100 ml water, the organic layer was evaporated under vacuum. The residue was chromatographed with dichloromethane/n-hexane (1:1) on silica gel (column=12×4 cm). The first eluted compound consisted of unchanged TPPN, crystallized from $CH_2Cl_2$/n-hexane affording 115 mg. Following evaporation of the solvent and crystallization of the residue of the next large fraction from $CH_2Cl_2$/n-hexane, the title compound was obtained in the form of small, blue needles having a melting point of 133°–135° C. Yield: 35 mg, 13.5 % (based on recovered TPPn: 38.4%).

Example 5—9-(N-BOC-6-aminocapronoxy)-2,7,12,17-tetra-n-propylporphycene

A solution of 239 mg (0.5 mmol) TPPn in 40 ml $CH_2Cl_2$ and 3 g N-BOC-6-aminocaproic acid was combined with 120 mg (0.5 mmol) $PbO_2$ and stirred for three days at room temperature. The reaction mixture was then poured into 200 ml water and extracted with 150 ml dichloromethane. After washing the organic phase once with 100 ml 5% aqueous sodium hydrogen carbonate and twice with 100 ml water, the organic layer was evaporated under vacuum. The residue was chromatographed with dichloromethane on silica gel (column =30×5 cm). The first eluted compound consisted of TPPn, crystallized from $CH_2Cl_2$/n-hexane affording 174 mg. Following evaporation of the solvent and crystallization of the residue of the next large fraction from $CH_2Cl_2$/n-hexane, the title compound was obtained in the form of small, blue needles having a melting point of 166°–168° C. Yield: 48.4 mg, 13.6% (based on recovered TPPn: 50%).

Example 6–9-(Chloroacetoxy)-2,7,12,17-tetra-n-propylporphycene

A solution of 96 mg (0.2 mmol) TPPn in 15 ml $CH_2Cl_2$ and 1 g chloroacetic acid was cooled to –70° C., combined with 24 mg (0.1 mmol) $PbO_2$ and stirred for one hour while warming up the mixture slowly to room temperature. The reaction mixture was treated with 40 ml $CH_2Cl_2$, then poured into 80 ml water and extracted with additional 50 ml dichloromethane. After washing the organic phase thrice with 80 ml water, the organic layer was evaporated under vacuum. The residue was chromatographed with $CH_2Cl_2$/n-hexane (1:2) on silica gel (column=20×4 cm). The first eluted compound consisted of unchanged TPPn, crystallized from $CH_2Cl_2$/n-hexane affording 78 mg. After evaporation of the solvent and crystallization the residue of the next large fraction from $CH_2Cl_2$/n-hexane, the title compound was obtained in the form of small, blue crystals having a melting point of 203°–204° C. Yield: 9.8 mg, 8.6% (based on recovered TPPn: 46%).

Example 7—9-(3-Bromopropionoxy)-2,7,12,17-tetra-n-propylporphycene

A solution of 96 mg (0. 2 mmol) TPPn in 15 ml $CH_2Cl_2$ and 1 g 3-bromopropionic acid was combined with 36 mg (0.15 mmol) $PbO_2$ and stirred for one hour at room temperature. The reaction mixture was treated with 40 ml $CH_2Cl_2$ and then poured into 80 ml of water and extracted with additional 50 ml of dichloromethane. After washing the organic phase once with 50 ml of 5% aqueous sodium hydrogen carbonate and twice with 50 ml water, the organic layer was evaporated under vacuum. The residue was chromatographed with dichloromethane/n-hexane (1:1) on silica gel (column=45×5 cm). The first eluted compound consisted of 17 mg unchanged TPPn, crystallized from $CH_2Cl_2$/n-hexane. Following evaporation of the solvent and crystallization the residue of the largest fraction from $CH_2Cl_2$/n-hexane, the title compound was obtained in the form of small, blue crystals having a melting point of 167°–169° C. Yield: 49 mg, 39% (based on recovered TPPn: 47%).

Example 8–9-Cinnamoxy-2,7,12,17-tetra-n-propylporphycene

A solution of 96 mg (0.2 mmol) TPPn in 10 ml $CH_2Cl_2$ and 0.5 g cinnamic acid was combined with 143 mg (0.6 mmol) $PbO_2$ and stirred for one day at room temperature. After conventional work up and chromatography as above with $CH_2Cl_2$/n-hexane (1:1) on silica gel, 48 mg unchanged TPPn and the title compound, in form of small, violet needles with a melting point of 220°–221° C., were obtained. Yield: 35 mg, 28% (based on recovered TPPn: 56%).

Example 9—9-(Succinoxy methylester)-2,7,12,17-tetra-n-propylporphycene

A solution of 96 mg (0.2 mmol) TPPn in 10 ml $CH_2Cl_2$ and 0.5 g succinic acid monomethylester was combined with 48 mg (0.2 mmol) $PbO_2$ and stirred for one day at room temperature. The reaction gave upon chromatography as described above, 30 mg unchanged TPPn and 26 mg 9-(succinoxy methylester)-tetra-n-propylporphycene in the form of small, blue needles having a melting point of 167°–168° C. Yield: 26 mg, 21.4 % (based on recovered TPPn: 31%).

Example 10—9-(Terephthaloxy methylester)-2,7,12,17-tetra-n-propylporphycene

A solution of 96 mg (0.2 mmol) TPPn in 10 ml $CH_2Cl_2$ and 0.5 g terephthalic acid monomethylester was combined with 287 mg (1.2 mmol) PbO$_2$ in small portions, stirred for 90 minutes at room temperature and then one hour at reflux. The reaction mixture was worked up and chromatographed as in previous examples on silica gel. After elution of unchanged TPPn affording 70.5 mg, the title compound was crystallized from CH$_2$Cl$_2$/n-hexane in the form of blue needles having a melting point of 244°–246° C. Yield: 15 mg, 11.4% (based on recovered TPPn: 43%).

Example 11—9-Anisoxy-2,7,12,17-tetra-n-propylporphycene

A solution of 96 mg (0.2 mmol) TPPn in 10 ml CH$_2$Cl$_2$ and 0.5 g anisic acid was combined with 382 mg (1.6 mmol) PbO$_2$ and stirred for one hour at reflux. The mixture was worked up and chromatographed with CH$_2$Cl$_2$/n-hexane (1:2) on silica gel (column =10×3 cm). Following evaporation of the solvent and crystallization of the residue of the large fractions, 46 mg unchanged TPPn from the first fraction and 22 mg of the title compound was obtained in the form of violet needles. The compound did not melt below 310° C. Yield : 22 mg, 17.5 (based on recovered TPPn: 33.6%).

Example 12—9-Amino-2,7,12,17-tetra-n-propylporphycene 478 mg (1 mmol) of tetra-n-propylporphycene were dissolved in 250 ml dichloromethane and 350 ml glacial acetic acid and combined with 680 mg (4 mmol) of finely ground AgNO$_3$. The stirred suspension was heated with reflux for 25–30 minutes. The reaction can be followed by means of thin layer chromatography (TLC: dichloromethane/n-hexane (1:3), silica gel). After cooling to room temperature, the insoluble material was removed and the solution was washed two times with water. The organic layer was brought to pH 6–6.5 with ice-cold 5% aqueous sodium hydroxide and finally washed with water. The raw product 9-nitro-tetra-n-propylporphycene was left in 300 ml dichloromethane, each combined with a solution of 40 g (1 mol) sodium hydroxide in 200 ml water and 36 g (0.2 mol) sodium dithionite in 200 ml water. The emulsion was refluxed under vigorously stirring for two hours (TLC: dichloromethane/n-hexane (1:1), silica gel). After cooling to room temperature and separating the two phases, the organic layer was washed three times with water and the organic solvent was evaporated under vacuum. The blue-green residue was recrystallized from dichloromethane/methanol to yield 420 mg (85%) 9-amino-tetra-n-propylporphycene in the form of very small, dark blue needles having a melting point of 220°–222° C.

Example 13—9-(Glutaric methylesteramide)-2,7,12,17-tetra-n-propylporphycene

To a solution of 98 mg (0.2 mmol) 9-amino-2,7,12,17-tetra-n-propylporphycene in 15 ml dry tetrahydrofuran and 15 ml dry pyridine was added at room temperature dropwise in 10 minutes by stirring a solution of 0.4 ml (2.89 mmol) glutaric methylester acid chloride in 10 ml dry tetrahydrofuran. The solution was stirred for an additional one hour at room temperature, diluted with tetrahydrofuran, cooled to 0° C. and treated with ice chilled water. The mixture was washed twice with 10% sulfuric acid, twice with water and once with 5% aqueous sodium hydrogencarbonate. After evaporation of the solvent of the separated organic layer, the residue was chromatographed with dichloromethane/ethyl acetate (6:1) on silica gel (column 20×4 cm). Following evaporation of the solvent under vacuum and crystallization of the residue of the main fraction from dichloromethane/hexane, the title compound 9-(glutaric methylesteramide)-2,7,12,17-tetra-n-propylporphycene was obtained in the form of violet needles having a melting point of 179°–180° C. Yield: 111 mg (90%).

Example 14—9-Glutaramide-2,7,12,17-tetra-n-propylporphycene 62 mg (0.1 mmol) 9-(glutaric methylesteramide)-2,7,12,17-tetra-n-propylporphycene were dissolved in 20 ml tetrahydrofuran, combined with 20 ml methanol and 12 ml of 4N aqueous sodium hydroxide were added dropwise while stirring at room temperature within 5 minutes. The reaction was stirred for an additional 45 minutes, neutralized and then precipitated under acidic conditions with the complete addition of ice-cold 150 ml 5% acetic acid. The flaky precipitate was filtered, washed with water, then with water/methanol (1:1) and dried. For recrystallization, the blue residue was redissolved in tetrahydrofuran, concentrated in vacuum, diluted with dichloromethane and treated with n-hexane. The title compound was obtained in the form of small, violet crystals which melt at 250°–251° C. with decomposition. Yield: 40 mg (66%).

Example 15—9-(5-Hydroxyvalerianamide)-2,7,12,17-tetra-n-propylporphycene

Under protective gas at 10° C., 45 mg (1.2 mmol) LiAlH$_4$ were added in small portions to a stirred solution of 62 mg (0.1 mmol) 9-(glutariomethylesteramide)-2,7,12,17-tetra-n-propylporphycene in 15 ml absolute tetrahydrofuran. The green mixture was stirred for 30 minutes at room temperature, then cooled to 0° C. and treated dropwise with 5 ml ethyl acetate, 5 ml of methanol and 5 ml glacial acetic acid. Insoluble material was removed by filtration and washed with tetrahydrofuran. The combined organic layers were washed twice with water and once with 5% aqueous sodium hydrogen carbonate. After evaporation of the solvent of the separated organic layer, the residue was chromatographed with dichloromethane/ethyl acetate (1:1) on silica gel (column 12×4 cm). Following evaporation of the solvent under vacuum and crystallization of the residue of the main fraction from tetrahydrofuran/hexane, the title compound 9-(5-hydroxyvalerianamide)-2,7,12,17-tetra-n-propylporphycene was obtained in the form of small, blue needles having a melting point of 221°–222° C. Yield: 38 mg (66%).

Example 16—9-(2-Acetoxyacetamide)-2,7,12,17-tetra-n-propylporphycene

To a solution of 98 mg (0.2 mmol) 9-amino-2,7,12,17-tetra-n-propylporphycene in 10 ml of dry tetrahydrofuran and 10 ml of dry pyridine was added at room temperature dropwise in 15 minutes, while stirring, a solution of 100 μl (0.9 mmol) acetoxy acetic acid chloride in 10 ml dry tetrahydrofuran. The solution was stirred for an additional 30 minutes at room temperature, diluted with tetrahydrofuran, cooled to 0° C. and treated with ice chilled water. The mixture was washed twice with 10% sulfuric acid, twice with water and once with 5% aqueous sodium hydrogen carbonate. After evaporation of the solvent of the separated organic layer, the residue was chromatographed with dichloromethane/ethyl acetate (4:1) on silica gel (column 15×4 cm). Following evaporation of the solvent under vacuum and crystallization of the residue of the main fraction from dichloromethane/hexane, the title compound was obtained in the form of small, blue needles having a melting point of 216°–218° C. Yield: 111 mg (93%).

Example 17—9-(2-Hydroxyacetamide)-2,7,12,17-tetra-n-propylporphycene 59 mg (0.1 mmol) 9-acetoxyacetamide-2,7,12,17-tetra-n-propylporphycene were dissolved in 30 ml of dry tetrahydrofuran and 3 ml of absolute methanol. While stirring at room temperature, 54 mg (1 mmol) sodium methoxide were added at once. The blue-green mixture was stirred for an additional 3 minutes, diluted with tetrahydrofuran, treated with ice chilled water and extracted thrice with dichloromethane. The combined organic layers were washed thrice with water. Following removal of the solvent under vacuum and recrystallization of the residue from tetrahydrofuran/hexane, the title compound 9-(2-hydroxyacetamide)-2,7,12,17-tetra-n-propylporphycene was obtained in the form of small, blue needles having a melting point of 300°–302° C. Yield: 51 mg (92%).

Example 18—4-(Methoxycarbonyl)benzyl triphenylphosphonium bromide 3.44 g (13 mmol) Triphenylphosphine were dissolved in 100 ml dry toluene, in a 250 ml flask with an argon feed. 3 g (13 mmol) 4-(bromomethyl)benzoic acid methyl ester were added, and the mixture was heated 2 hr at reflux, with stirring. The white phosphonium salt which precipitated was separated out from the cooled mixture, washed with absolute toluene, and dried in a vacuum. The fine crystals melted at 251°–252° C. Yield: 5.85 g (91%).

Example 19—4-(β-Apo-7'-carotenyl)benzoic acid methyl ester 860 mg (1.8 mmol) 4-(methoxycarbonyl)benzyl triphenylphosphonium bromide, 173 mg (3.2 mmol) sodium methanolate, and 500 mg (1.2 mmol) β-apo-8'-carotenal were dissolved in 25 ml absolute toluene. The dark-colored liquid was heated 3 hr at reflux. The course of the reaction was monitored by thin layer chromatography (silica gel with dichloromethane:ethyl acetate 5:1); additionally, there were added 500 mg (1 mmol) of the phosphonium bromide and 100 mg (1.8 mmol) sodium methanolate. After an additional 4–5 hr under reflux, the completely reacted mixture was cooled, diluted with 150 ml dichloromethane, and extracted 3 times with 150 ml aliquots of water. The organic phase was dried over magnesium sulfate, the solvent was removed under vacuum, and the reddish-brown residue was chromatographed with dichloromethanemethyl acetate 5:1 over silica gel, under inert conditions (column: 15×4 cm). Following a red forerun, the orange main fraction was eluted, from which 405 mg (61%) of the carotenoid methyl ester was obtained following evaporation of eluent under vacuum and recrystallization from dichloromethane/hexane. The red crystals had a melting point of 168°–170° C.

Example 20—4-(β-Apo-7'-carotenyl)benzoic acid 6 ml 5N sodium hydroxide was added to a solution of 220 mg (0.4 mmol) 4-(β-Apo-7'-carotenyl)-benzoic acid methyl ester in 40 ml tetrahydrofuran and 10 ml methanol, and the mixture was stirred 12 hr at room temperature, under light protection and under an argon atmosphere. The mixture was cooled, brought to pH 1–2 with 5% sulfuric acid, and extracted 3 times with dichloromethane. The combined organic phases were washed twice with water, dried over sodium sulfate, and vacuum distilled to remove the solvent. The yield of orangeish-red carotenoid carboxylic acid was 200 mg (92%).

Recrystallization from dichloromethane:hexane yielded fine, red crystals which melted at 230°–232° C.

Example 21—4-(β-Apo-7'-carotenyl)benzoyl chloride 80 mg (0.15 mmol) 4-(β-Apo-7'-carotenyl)benzoic acid was dissolved in 4 ml absolute toluene and 2 ml absolute pyridine. 55 μl (0.75 mmol) Thionyl chloride in 3 ml absolute toluene was added dropwise to this mixture, and stirring was continued 10–12 min at room temperature. Then the solvent mixture and excess thionyl chloride were removed by water flow aspiration, over a water bath at 18°–22° C., and the remaining reddish-brown acid chloride was absorbed in 5 ml absolute tetrahydrofuran.

Example 22—9-(4-(β-Apo-7'-carotenyl)benzoyloxy)-2,7,12,17-tetra-n-propylporphycene The acid chloride solution of Example 11 is added dropwise to a solution of 9-hydroxy-2,7,12,17-tetra-n-propylporphycene (0.1 mmol) in 5 ml tetrahydrofuran and 3 ml absolute pyridine, and the mixture is stirred an additional 1 hr at room temperature. The mixture is diluted with 100 ml dichloromethane, hydrolyzed with ice water, and extracted twice with fresh portions of ice-cold 10% sulfuric acid. After washing the organic phase with 5% sodium hydrogen carbonate solution and then water, the solvent is removed under vacuum. The residue obtained is then chromatographed. The product fraction is eluted and the title compound is obtained after evaporation of the eluent and recrystallization.

Example 23—9-(4-β-Apo-7'-carotenyl)benzamido)-2,7,12,17-tetra-n-propylporphycene The solution of the carotenyl acid chloride of Example 11 is added dropwise to a solution of 9-amino-2,7,12,17-tetra-n-propylporphycene (0.1 mmol) in 5 ml absolute tetrahydrofuran and 3 ml absolute pyridine, and the mixture is stirred an additional 1 hr at room temperature. The mixture is diluted with 100 ml dichloromethane, hydrolyzed with ice water, and extracted twice with ice-cold 10% sulfuric acid. After washing the organic phase with 5% sodium hydrogen carbonate solution and then water, the solvent is removed under vacuum. The residue obtained is the chromatographed. The product fraction is eluted and the title compound is obtained after evaporation of the eluent and recrystallization.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A porphycene of the formula:

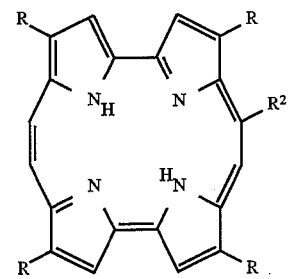

wherein:
 each R is, independently, hydrogen, alkyl, aralkyl or aryl; and $R^2$ is:
(1) $OCOR^3$, wherein $R^3$ is —$(CH_2)_m$—Y, m=1–10 and Y is:
  (a) $C(O)OR^4$, wherein $R^4$ is hydrogen, alkyl, aryl, aralkyl, cycloalkyl or cycloalkylalkyl; or
  (b) $NHC(O)OR^4$, wherein $R^4$ is as defined above;
or
(2) $OC(O)R^7$, wherein $R^7$ is aryl substituted with 1–3 haloalkyl, cyano, $C_{1-6}$ alkoxy or $C_{2-6}$ alkoxycarbonyl groups or —$CHR^8$=$CHR^9$—$R^{10}$ is alkyl, aryl, aralkyl, cycloalkyl or cycloalkylalkyl;
or a salt or metal complex thereof.

2. The porphycene of claim 1, wherein $R^2$ is $OCO(CH_2)_m$—Y, m=1–6 and Y is $C(O)OR^4$, where $R^4$ is H or $C_{1-6}$ alkyl.

3. A porphycene of the formula:

wherein:
each R is, independently, hydrogen, alkyl, aralkyl or aryl; and
$R^2$ is
(a) $NHC(O)OR^4$, wherein $R^4$ is hydrogen, alkyl, aryl, aralkyl, cycloalkyl or cycloalkylalkyl; or
(b) NHCO—$(CH_2)_p$—Z or NHCO—$O(CH_2)_p$—Z, wherein p=1–10 and Z is OH, $NR^{11}R^{12}$, $C(O)OR^4$, $OC(O)R^4$, $C(O)NHR^4$ or $NHC(O)OR^4$, wherein $R^4$ is as defined above, and $R^{11}$ and $R^{12}$ are independently cycloalkyl or cycloalkylalkyl groups;
or a salt or metal complex thereof.

4. The porphycene of claim 3, wherein R is $(CH_2)_n$—H and n=1–10.

5. The porphycene of claim 3, wherein $R^2$ is a group of the formula NHCO—$(CH_2)_p$—Z or NHCO—$O(CH_2)_p$—Z, where p=1–10 and Z is $NR^{11}R^{12}$, $C(O)OR^4$, $OC(O)R^4$, $C(O)NHR^4$ or $NHC(O)OR^4$.

6. The porphycene of claim 1, wherein R is $(CH_2)_n$—H and n=1–10.

7. The porphycene of claim 1, wherein $R^2$ is —$OCOR^3$, $R^3$ is $(CH_2)_m$—Y, m=1–6, Y is a $COOR^4$, and $R^4$ is $C_{1-6}$ alkyl.

8. The porphycene of claim 1, wherein $R^2$ is —$OCOR^3$, $R^3$ is $(CH_2)_m$—Y, m=1–6, Y is $NR^5R^4$ or $NR^4$ or $NR^4R^5R^{6+}A^-$ and $R^4$, $R^5$ and $R^6$ are H or $C_{1-6}$ alkyl.

9. The porphycene of claim 1, wherein $R^2$ is —$OCOR^3$, $R^3$ is $(CH_2)_m$—Y, m=1–6, Y is NH—$C(O)OR^4$, and $R^4$ is $C_{1-6}$ alkyl.

10. The porphycene of claim 1, wherein $R^2$ is —NHCO$(CH_2)_p$—Z or —$NH(CH_2)_{p+1}$—Z, p=1–6 and Z is OH, $OCOR^4$ or $C(O)OR^4$, wherein $R^4$ is H or $C_{1-6}$ alkyl.

11. The porphycene of claim 7, wherein $R^2$ is —NHCO$(CH_2)_p$—Z, p=1 and Z is OH.

12. The porphycene of claim 1, wherein $R^2$ is —NHCO$(CH_2)_p$—Z or —$NH(CH_2)_{p+1}$—Z, p=1–6 and Z is $NH_2$ or $NHC(O)OR^4$, wherein $R^4$ is H or $C_{1-6}$ alkyl.

13. A pharmaceutical composition comprising an effective amount of the porphycene of claim 1 and a pharmaceutically acceptable carrier.

14. The pharmaceutical composition of claim 13, wherein said porphycene is incorporated within liposomes.

15. The pharmaceutical composition of claim 13, wherein said composition comprises a dispersion.

16. The pharmaceutical composition of claim 13, wherein said composition comprises a solution.

17. A method of photodynamic therapy, comprising and administering to a patient in need thereof an effective amount of the porphycene of claim 1.

18. The porphycene of claim 3, wherein $R^2$ is —NHCO$(CH_2)_p$—Z, p=1–6 and Z is OH, $OCOR^4$ or $C(O)OR^4$, where $R^4$ is H or $C_{1-6}$ alkyl.

19. The porphycene of claim 4, wherein $R^2$ is —NHCO$(CH_2)_p$—Z, p=1–6 and Z is $C(O)OR^4$, where $R^4$ is H or $C_{1-6}$ alkyl.

20. The porphycene of claim 18, wherein each R is n-propyl and $R^4$ is H.

21. A pharmaceutical composition comprising an effective amount of the porphycene of claim 3 and a pharmaceutically acceptable carrier.

22. The pharmaceutical composition of claim 21, wherein said porphycene is incorporated within liposomes.

23. The pharmaceutical composition of claim 21, wherein said composition comprises a dispersion.

24. The pharmaceutical composition of claim 21, wherein said composition comprises a solution.

25. A method of photodynamic therapy, comprising and administering to a patient in need thereof an effective amount of the pharmaceutical composition of claim 21.

* * * * *